(12) United States Patent
Craig

(10) Patent No.: US 6,986,776 B2
(45) Date of Patent: Jan. 17, 2006

(54) SUTURING APPARATUS, METHOD AND SYSTEM

(76) Inventor: H. Randall Craig, 3200 N. Dobson Rd. #F7, Chandler, AZ (US) 85224

( * ) Notice: Subject to any disclaimer, the term of this patent is extended or adjusted under 35 U.S.C. 154(b) by 157 days.

(21) Appl. No.: 10/064,235

(22) Filed: Jun. 24, 2002

(65) Prior Publication Data

US 2003/0009179 A1    Jan. 9, 2003

Related U.S. Application Data

(60) Provisional application No. 60/302,338, filed on Jun. 28, 2001.

(51) Int. Cl.
*A61B 17/04* (2006.01)

(52) U.S. Cl. ............... 606/148; 606/139; 606/222; 606/223

(58) Field of Classification Search ........ 606/148, 606/139, 144, 222, 223; 49/419; 81/3.07–34.9; 30/130; 289/17; 112/169, 222
See application file for complete search history.

(56) References Cited

U.S. PATENT DOCUMENTS

| | | | | |
|---|---|---|---|---|
| 102,348 A | * | 4/1870 | Willard | 99/419 |
| 629,003 A | * | 7/1899 | Cox | 294/10 |
| 1,534,202 A | * | 4/1925 | Boley et al. | 30/150 |
| 2,181,081 A | * | 11/1939 | Ganaway | 356/247 |
| 2,498,155 A | * | 2/1950 | De Jonge | 42/111 |
| 2,634,674 A | * | 4/1953 | Irwin | 99/419 |
| 3,063,360 A | * | 11/1962 | Fitch et al. | 99/419 |
| 3,758,143 A | * | 9/1973 | Godlewski | 294/8 |
| 3,827,685 A | * | 8/1974 | Wennes | 269/229 |
| 3,858,933 A | * | 1/1975 | Koehring | 297/463.1 |
| 3,964,173 A | * | 6/1976 | Atchisson | 42/136 |
| 4,460,147 A | * | 7/1984 | Macbain | 248/542 |
| 4,817,514 A | * | 4/1989 | Hitch et al. | 99/419 |
| 4,874,156 A | * | 10/1989 | Goldzweig | 269/158 |
| 4,919,929 A | * | 4/1990 | Beck | 424/157.1 |
| 5,018,530 A | | 5/1991 | Rank | |
| 5,330,503 A | | 7/1994 | Yoon | |
| 5,356,424 A | | 10/1994 | Buzerak et al. | |
| 5,368,595 A | | 11/1994 | Lewis | |
| 5,405,376 A | | 4/1995 | Mulier | |
| 5,423,836 A | | 6/1995 | Brown | |
| 5,499,990 A | | 3/1996 | Schulken et al. | |
| 5,545,148 A | | 8/1996 | Wurster | |
| 5,562,685 A | | 10/1996 | Mollenauer | |
| 5,582,616 A | | 12/1996 | Bolduc et al. | |
| 5,636,984 A | * | 6/1997 | Gomes | 433/30 |
| 5,662,683 A | | 9/1997 | Kay | |

(Continued)

*Primary Examiner*—Anhtuan T. Nguyen
*Assistant Examiner*—Michael G. Mendoza
(74) *Attorney, Agent, or Firm*—Oppedahl & Larson LLP

(57) ABSTRACT

An apparatus used with a helical suture device has a first end and a second end. The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

18 Claims, 5 Drawing Sheets

U.S. PATENT DOCUMENTS

| | | |
|---|---|---|
| 5,695,462 A | 12/1997 | Sutco et al. |
| 5,709,692 A | 1/1998 | Mollenauer et al. |
| 5,797,928 A * | 8/1998 | Kogasaka .................. 606/144 |
| 5,820,631 A | 10/1998 | Nobles |
| 5,947,983 A | 9/1999 | Solar et al. |
| 6,086,601 A * | 7/2000 | Yoon ........................... 606/148 |
| 6,131,361 A * | 10/2000 | Murphy ....................... 52/712 |
| 6,626,917 B1 | 9/2003 | Craig |
| 6,663,633 B1 * | 12/2003 | Pierson, III .................. 606/72 |
| 2001/0045753 A1 * | 11/2001 | Lewis ........................... 294/3 |

\* cited by examiner

SUTURING APPARATUS, METHOD AND SYSTEM

CROSS REFERENCE TO RELATED APPLICATIONS

This application claims priority from U.S. application Ser. No. 60/302,338 filed Jun. 28, 2001, which application is incorporated herein by reference.

BACKGROUND OF THE INVENTION

The invention relates generally to suturing and relates more particularly to suturing in which it is desired to suture a layer of tissue without puncturing or damaging another layer of tissue.

It is well known to suture tissue, for example to close wounds and incisions in living tissue. Some historical background of suturing is found in PCT appl. no. PCT/US00/29508, filed Oct. 26, 2000, designating the United States, published as PCT publication no. WO 01/30245, published May 3, 2001 and assigned to the same assignee as the assignee of the present application, incorporated herein by reference.

One goal in suturing is to bring two tissue edges together by means of the sutures. It is also typically desired that the sutures not puncture a deeper tissue. It is also typically desired that the points at which the sutures puncture the tissue be in a particular relationship with the tissue edges. For example, it is typically desired that the points not be too close to the edges. Competing with the latter goal is the previously mentioned goal that the suture not puncture the deeper tissue.

It is also known to perform a series of sutures with the assistance of a helical suture device such as that set forth in the above-mentioned PCT application designating the United States. With such a helical suture device, it is necessary to draw some balance between large and small diameters. If the diameter is too small, the punctures may be undesirably close to the edges of the tissue being sutured. If the diameter is too large, there is the concern that the suture device may undesirably pierce the tissue below would thus be extremely desirable if a way could be devised in which a helical suture device could be employed to suture tissue, while minimizing the risk that the device may puncture tissue below.

SUMMARY OF INVENTION

An apparatus used with a helical suture device has a first end and a second end. The first end includes a spatulate member having a length along a first axis. The second end includes a guide shaped to receive a cylindrical axle of the helical suture device for rotation on a second axis. The guide is shaped to constrain the first axis in fixed position relative to the second axis, the first and second axes each lying within a plane. The spatulate member extends, typically symmetrically, in a first direction and a second direction from the first axis, the first direction and second direction being on opposite sides of the plane. The apparatus lies between a first tissue that is to be sutured, and a second tissue that is desired not to be sutured.

BRIEF DESCRIPTION OF DRAWINGS

The invention is described with respect to a drawing in several figures, of which.

Where possible, like reference designations have been used among the figures to designate like features.

DETAILED DESCRIPTION

The present invention, a tissue shield, in combination with a helical suturing instrument, results in the placement of a continuous suture with substantially increased efficiency, and with a minimized risk of inadvertently puncturing or damaging underlying or surrounding tissue.

Figure 1:
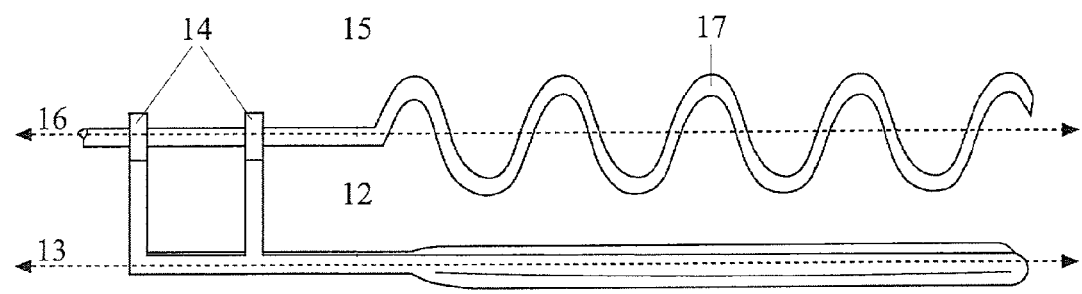
FIG. 1 is a side view of an embodiment of a tissue shield and helical suture instrument.
Figure 2:
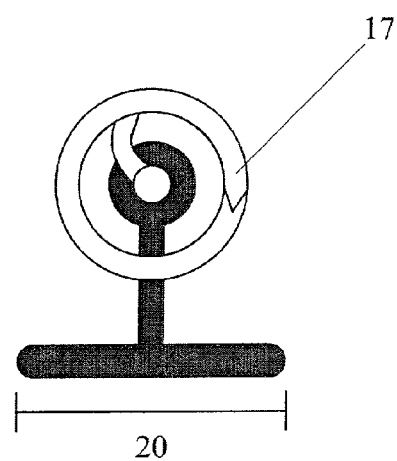
FIG. 2 is a front view of an embodiment of a spatulate member of a tissue shield and a helical suture instrument.

A first embodiment of the invention is the tissue shield itself, which comprises an apparatus having a first end 11 and a second end 12, as illustrated in FIG. 1. The first end comprises a spatulate member having a length, an embodiment of which may be greater than one inch and less than seven inches, along a first axis 13. As illustrated in FIG. 2, the spatulate member extends in a first direction and a second direction from the first axis 13, the first direction and second direction are on opposite sides of the plane. The extensions in the first and second direction from the first axis define a width 20. In an exemplary embodiment, the width defined by the extensions is less than one third of the length. It is not required, but the spatulate member may be symmetric relative to the first axis.

Figure 3:
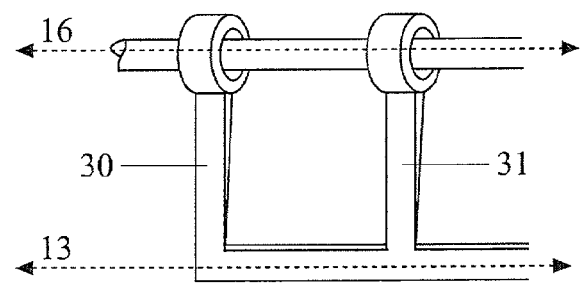
FIG. 3 is an embodiment of a guide from a tissue shield.

The second end comprises a guide 14 shaped to receive a cylindrical axle 15 for rotation on a second axis 16. A possible configuration for the guide is illustrated in FIG. 3. Here the guide comprises two members 30 and 31. Each member extends toward the second axis 16 from the first axis 13. Each of the members has a hole shaped to receive the cylindrical axle as defined below. The guide is shaped to constrain the first axis in fixed position relative and substantially parallel to the second axis, the first and second axes each lying within a plane. For this embodiment of the invention, the terms "substantially parallel" mean that the axes may be constrained to be within 15 degrees of parallel. Alternatively, the confinement angle could be 10 degrees or 5 degrees. An exemplary embodiment of this configuration is where the first and second axes are greater than one-quarter inch apart.

As shown in FIG. 1, the cylindrical axle 15 is a straight portion of a tubular member of a helical suture instrument 17 such as the one disclosed in PCT appl. no. PCT/US00/29508 published as PCT publication no. WO 01/30245. The cylindrical axle 15 is inserted into the guide for support purposes during suturing and to help prevent the tissue shield from separating from the helical suture needle. Stated differently, the guide keeps the shield positioned reliably relative to the helical suture instrument.

Figure 4:
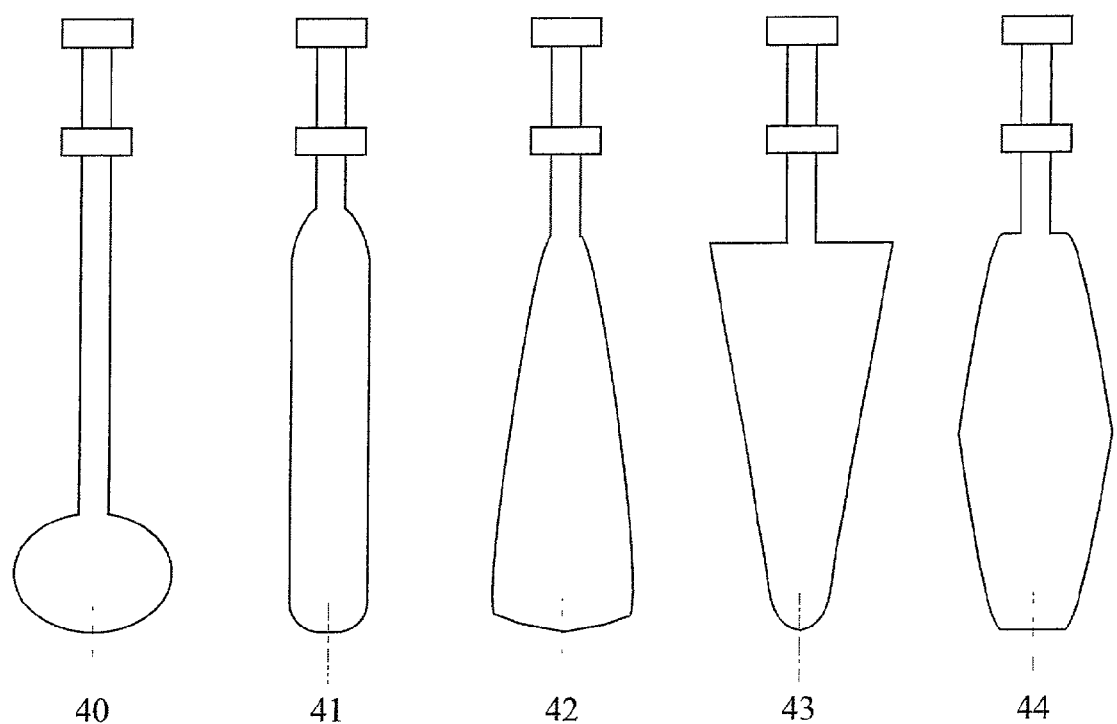
FIG. 4 is a top view of several embodiments of spatulate members.
Figure 5:
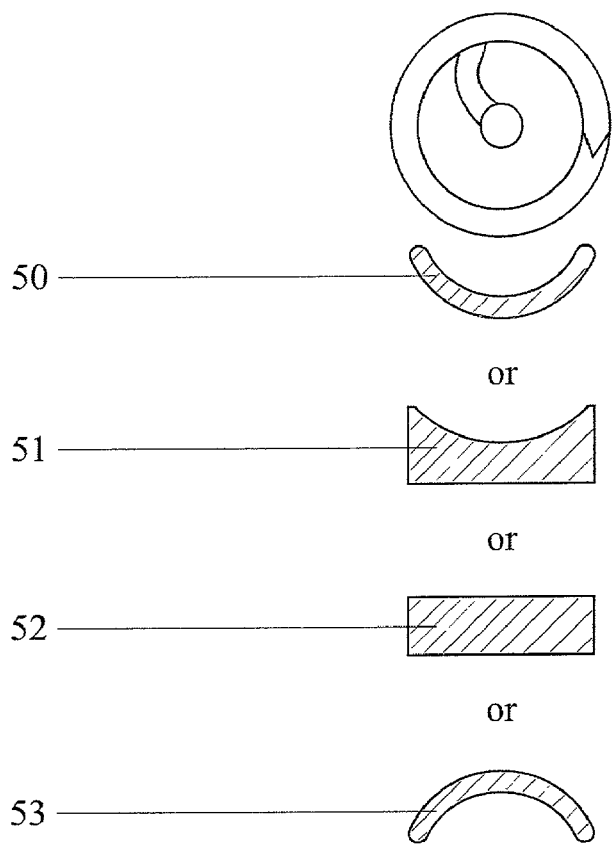
FIG. 5 is a front view of several embodiments of spatulate members.

Depending on the type and location of tissue requiring suturing, one may desire a variety of different shapes for the spatulate member of the tissue shield. Most shapes are symmetric about the first axis 13, however, this symmetry is not required. Several examples of top views of potential shapes for the spatulate member are illustrated in FIG. 4. These shapes include but are not limited to: a "T-shape" 40 which has a long skinny section with an oval shape at the end whose major axis is perpendicular to first axis 13; a "Blade" shape 41 which is a rectangle with rounded corners, a "Tapered" shape 42 which looks like a teardrop having its narrowest point at the end closest to the guide, a "Pointed" shape 43 which resembles a triangle with rounded corners having a base at the end closest to the guide, and a "Flared" shape 44 which resembles a hexagon with rounded corners. Many other shapes are possible, especially polygons with rounded corners as well as circular or elliptical shapes with continuous curves. While it is not required, it is preferred that the corners on any polygon are rounded to prevent tissue damage from sharp edges. Addition to the variations in the potential top views of the spatulate member, the member may also have differences in the surface that is located just below where a helical suture may be present. This again depends on tissue requirements or application. Several examples of potential cross sections of the tissue shields show these various shapes and are illustrated in FIG. 5. These surface shapes include but are not limited to: a surface concave about first axis 13 and a helical suturing device 50; a surface concave about first axis 13 and a helical suturing device, but having a flat base 51; a completely flat surface 52; a surface convex about first axis 13 and a helical suturing device 53; and a surface convex about first axis 13 and a helical suturing device, but having a flat base.

Figure 6:
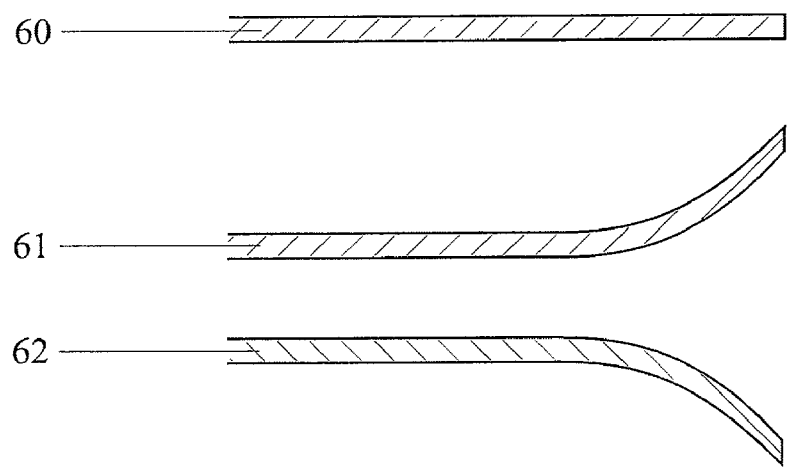
FIG. 6 is a side view of several embodiments of spatulate members.

The spatulate member of the tissue shield has a leading edge which is on the end located under a helical suture needle tip as disclosed in PCT appl. no. PCT/US00/29508 published as PCT publication no. WO 01/30245. This edge may or may not be flat 60 depending on the tissue to be sutured. It also may have, but is not limited to a leading edge that is curved upward 61 toward second axis 14 or an edge that is curved downward 62 away from the second axis 14. These general examples are illustrated in FIG. 6.

The apparatus of the tissue shield invention may be made of plastic, metal or other sufficiently hard materials. A suitable material may be non-porous to simplify sterilization. It should be stiff enough to not deform unduly when pressed against various tissue, but not so stiff that it is brittle and likely to crack or break during a procedure.

Ideally, any instrument used in a surgical or other invasive procedure is desired to be sterile. This also holds true for the tissue shield. Although it is not required during the manufacture of the invention, the shield may be sterilized be methods including but not limited to: toxic gas, heat, boiling, and gamma radiation. If the invention is sterilized during manufacture or packaging, it may be desirable to enclose the apparatus in a protective wrapper that will assist in the preservation of sterility. Whether or not the tissue shield is to be sterilized during manufacture, it is desirable that the surface of the tissue protector be extremely smooth to help aid in any sterilization process.

A second embodiment of the invention is a helical suture instrument 10 (FIG. 1) as disclosed in PCT appl. no. PCT/US00/29508 published as PCT publication no. WO 01/30245 and tissue protecting apparatus as described above. The helical suture instrument has a cylindrical axle which defines the second axis, and a helical portion having a helical outer diameter. The helical suture instrument also has second axial length along the second axis. More descriptive detail is provided in the above referenced PCT application.

Figure 7:
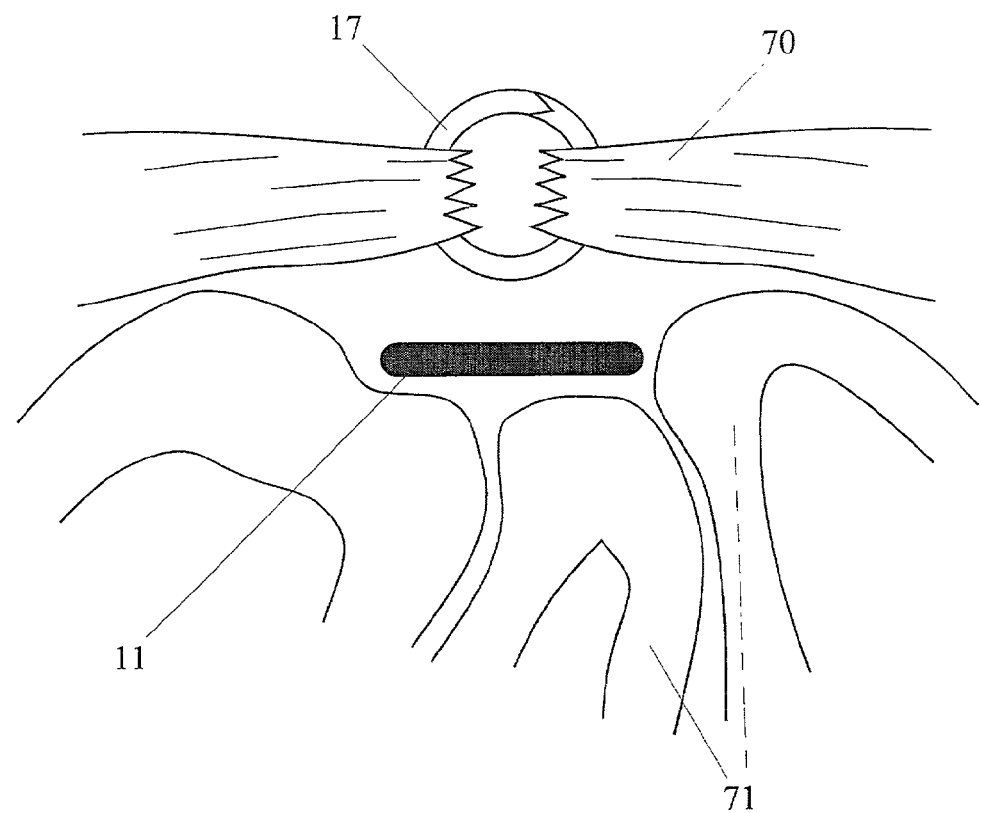
FIG. 7 is an illustration of the tissue shield and helical suturing instrument may be placed during use.
Figure 8:
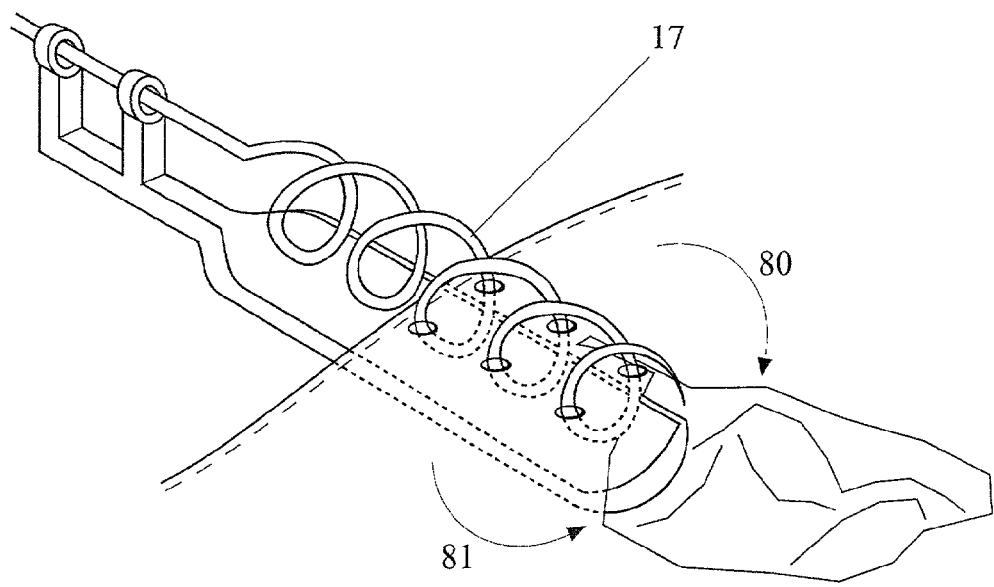
FIG. 8 is an illustration of a helical suturing instrument in use.
Figure 9:
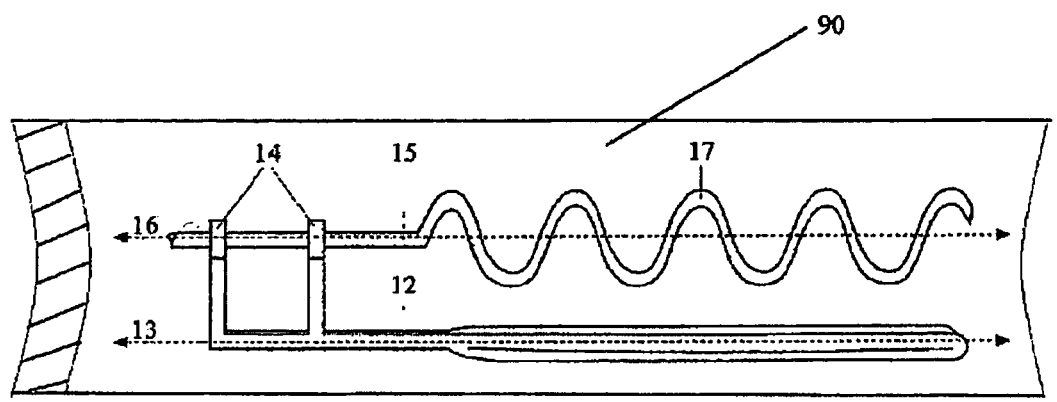
FIG. 9 is an illustration of the helical suture instrument and apparatus contained in a wrapper.

A suturing method performed with the apparatus of the helical suture needle and tissue shield described above comprises the following steps. First the spatulate member is placed between the first and second tissues. The first tissue 70 is the tissue desired to be sutured, and the second tissue 71 is the tissue requiring protection from becoming damaged during the procedure. See FIG. 7 for an illustration of placement of the system. The second step is to rotate the helical suture instrument in a first direction 80 to pierce alternately the first and second edges of the first tissue. This direction may be clockwise or counterclockwise depending on the position of the sharp end of the helical suture needle and the direction of its turns. See FIG. 8 for an illustration of this process. The third step is to rotate the helical suture instrument in a second direction 81, which is the opposite of the first, to withdraw the helical suture instrument from the first tissue. The final step is to withdraw the spatulate member from between the first and second tissues as the helical suture instrument is rotated in the second direction.

What is claimed is:

1. A system comprising a helical suture instrument and apparatus having
    a first end and a second end, the first end comprising a spatulate member having a first length along a first axis;
    the helical suture instrument having a cylindrical axle defining a second axis and a helical portion, the helical portion having a helical outer diameter and having a second axial length along the second axis, the second end of the apparatus comprising a guide shaped to receive the cylindrical axle for rotation on the second axis, the guide shaped to constrain the first axis in fixed position relative to the second axis, the first and second axes each lying within a plane and constrained to lie within that plane;
    the spatulate member extending in a first direction and a second direction from the first axis, the first direction and second direction being on opposite sides of the plane; wherein the first and second axes are farther apart than the helical outer diameter, whereby there is space between the helical portion and the apparatus;
    wherein the first length is at least five-sixths of the second length.

2. The system of claim 1 wherein the first length is greater than the second length.

3. The system of claim 1 wherein the guide comprises two members each extending toward the second axis from the first axis, each of the two members having a hole shaped to receive the cylindrical axle.

4. The system of claim 1, further characterized in that the extensions in the first and second directions define a width, the width being less than one-third of the first length.

5. The system of claim 1 wherein the spatulate member is symmetric relative to the first axis.

6. The system of claim 1 further characterized as being sterile.

7. A system comprising a helical suture instrument and apparatus having
    a first end and a second end, the first end comprising a spatulate member having a first length along a first axis;
    the helical suture instrument having a cylindrical axle defining a second axis and a helical portion, the helical portion having a helical outer diameter and having a second axial length along the second axis, the helical portion surrounding an open helical center, the second end of the apparatus comprising a guide shaped to receive the cylindrical axle for rotation on the second axis, the guide shaped to constrain the first axis in fixed position relative to the second axis, the first and second axes each lying within a plane and constrained to lie within the plane;

the spatulate member extending in a first direction and a second direction from the first axis, the first direction and second direction being on opposite sides of the plane;

wherein the first and second axes are farther apart than the helical outer diameter, whereby there is space between the helical portion and the apparatus;

wherein the first length is at least five-sixths of the second length.

8. A system comprising a helical suture instrument and apparatus having a first end and a second end, the first end comprising a spatulate member having a first length along a first axis;

the helical suture instrument having a cylindrical axle defining a second axis and a helical portion, the helical portion having a helical outer diameter and having a second axial length along the second axis, the second end of the apparatus comprising a guide shaped to receive the cylindrical axle for rotation on the second axis, the guide shaped to constrain the first axis in fixed position relative to the second axis, the first and second axes each lying within a plane;

the spatulate member extending in a first direction and a second direction from the first axis, the first direction and second direction being on opposite sides of the plane;

wherein the first and second axes are farther apart than the helical outer diameter, whereby there is space between the helical portion and the apparatus; wherein the first length is at least five-sixths of the second length.

9. A system comprising a helical suture instrument and apparatus having a first end and a second end, the first end comprising a spatulate member having a first length along a first axis;

the helical suture instrument having a cylindrical axle defining a second axis and a helical portion, the helical portion having a helical outer diameter and having a second axial length along the second axis, the helical portion surrounding an open helical center, the second end of the apparatus comprising a guide shaped to receive the cylindrical axle for rotation on the second axis, the guide shaped to constrain the first axis in fixed position relative to the second axis, the first and second axes each lying within a plane;

the spatulate member extending in a first direction and a second direction from the first axis, the first direction and second direction being on opposite sides of the plane; wherein the first and second axes are farther apart than the helical outer diameter, whereby there is space between the helical portion and the apparatus; wherein the first length is at least five-sixths of the second length.

10. A helical suture instrument and apparatus having a first end and a second end, the first end comprising a spatulate member having a first length along a first axis;

the helical suture instrument having a cylindrical axle defining a second axis and a helical portion, the helical portion having a helical outer diameter and having a second axial length along the second axis, the second end of the apparatus comprising a guide shaped to receive the cylindrical axle for rotation on the second axis.

11. An apparatus having a first end and a second end, the first end comprising a spatulate member having a length along a first axis; the second end comprising a guide shaped to receive a cylindrical axle for rotation on a second axis, the guide shaped to constrain the first axis in fixed position relative to the second axis, the first and second axes constrained to lie within a single plane;

the spatulate member extending in a first direction and a second direction from the first axis, the first direction and second direction being on opposite sides of the plane;

wherein the first and second axes are more than one-quarter inch apart and less then an inch apart.

12. An apparatus having a first end and a second end, the first end comprising a spatulate member having a length along a first axis;

the second end comprising a guide shaped to receive a cylindrical axle for rotation on a second axis, the guide shaped to constrain the first axis in fixed position relative to the second axis, the first and second axes constrained to lie within a single plane; the spatulate member extending in a first direction and a second direction from the first axis, the first direction and second direction being on opposite sides of the plane, wherein the length of the spatulate member is greater than one inch and less then seven inches.

13. An apparatus having a first end and a second end, the first end comprising a spatulate member having a length along a first axis;

the second end comprising a guide shaped to receive a cylindrical axle for rotation on a second axis, the guide shaped to constrain the first axis in fixed position relative to the second axis, the first and second axes constrained to lie within a single plane;

the spatulate member extending in a first direction and a second direction from the first axis, the first direction and second direction being on opposite sides of the plane;

further characterized in that the extensions in the first and second directions define a width, the width being less than one-third of the length.

14. The system of claim 8 wherein the first length is greater than the second length.

15. The system of claim 8 wherein the guide comprises two members each extending toward the second axis from the first axis, each of the two members having a hole shaped to receive the cylindrical axle.

16. The system of claim 8, further characterized in that the extensions in the first and second directions define a width, the width being less than one-third of the first length.

17. The system of claim 8 wherein the spatulate member is symmetric relative to the first axis.

18. The system of claim 8 further characterized as being sterile.

* * * * *